(12) United States Patent
Kanou et al.

(10) Patent No.: US 6,838,883 B2
(45) Date of Patent: Jan. 4, 2005

(54) METHOD AND SYSTEM FOR MONITORING STATE OF LEAD ACID BATTERY

(75) Inventors: Tetsuya Kanou, Fukushima (JP); Yuichi Watakabe, Tochigi (JP); Koji Miyata, Tochigi (JP); Kiyoshi Takahashi, Tochigi (JP); Masanobu Narita, Tochigi (JP)

(73) Assignee: The Furukawa Battery Co., Ltd., Yokohama (JP)

( * ) Notice: Subject to any disclaimer, the term of this patent is extended or adjusted under 35 U.S.C. 154(b) by 51 days.

(21) Appl. No.: 10/287,798

(22) Filed: Nov. 5, 2002

(65) Prior Publication Data

US 2004/0085072 A1 May 6, 2004

(51) Int. Cl.[7] .............................................. G01N 27/02
(52) U.S. Cl. ....................................................... 324/439
(58) Field of Search ................................ 320/118, 116, 320/124, 125, 127, 128, 132, 134, 136, 137; 324/426, 427, 430

(56) References Cited

U.S. PATENT DOCUMENTS 6,313,607 B1 * 11/2001 Champlin .................... 324/430
6,469,471 B1 * 10/2002 Anbuky et al. .............. 320/118
6,495,990 B2 * 12/2002 Champlin .................... 320/132
6,597,150 B1 * 7/2003 Bertness et al. ............. 320/104

FOREIGN PATENT DOCUMENTS

| JP | 6-194428 | 7/1994 |
| JP | 11-7985 | 1/1999 |

OTHER PUBLICATIONS

David Linden, Hanbook of Batteries, Second Edition 1995, pp. 2.25–2.27, and 24.39–24.40.*

* cited by examiner

*Primary Examiner*—Pia Tibbits
(74) *Attorney, Agent, or Firm*—McGinn & Gibb, PLLC

(57) ABSTRACT

In order to monitor a state of a battery, a threshold value of an internal impedance of the battery is first determined. It is prepared an approximate expression indicating a correlation between a residual capacity of the battery and an internal impedance of the battery which is greater than the threshold value. The internal impedance of the battery is then measured. When the measured internal impedance is the threshold value or less, the residual capacity is determined as an initial value. When the measured internal impedance is greater than the threshold value, the residual capacity is monitored with the approximate expression.

40 Claims, 14 Drawing Sheets

FIG. 14

| YEARS | BATTERY 1 | | | BATTERY 2 | | | BATTERY 3 | | |
|---|---|---|---|---|---|---|---|---|---|
| | INTERNAL IMPEDANCE | CHANGING RATE (%) | RESIDUAL CAPACITY (%) | INTERNAL IMPEDANCE | CHANGING RATE (%) | RESIDUAL CAPACITY (%) | INTERNAL IMPEDANCE | CHANGING RATE (%) | RESIDUAL CAPACITY (%) |
| 6 | 120 | | | 147 | | | 105 | | |
| 6.5 | 126 | 105.0 | | 157 | 106.8 | 96 | 107 | 101.9 | 104 |
| 7 | 132 | 104.8 | 100 | 170 | 108.3 | 93 | 110 | 102.8 | 103 |
| 7.5 | 142 | 107.5 | 94 | 187 | 110.0 | 83 | 115 | 104.5 | 100 |
| 8 | 154 | 108.5 | 89 | 210 | 112.3 | 69 | 125 | 108.7 | 85 |
| 8.5 | 168 | 109.1 | 83 | | | | 139 | 111.2 | 76 |
| 9 | 188 | 111.9 | 65 | | | | 169 | 121.6 | |
| 9.5 | 220 | 114.6 | | | | | | | |
| 10 | | | | | | | | | |

METHOD AND SYSTEM FOR MONITORING STATE OF LEAD ACID BATTERY

BACKGROUND OF THE INVENTION

This invention relates to a method for monitoring the state of a lead acid battery such as the residual capacity, the residual lifetime or the like by measuring an internal impedance of the lead acid battery.

Hitherto, a lead acid battery has been used as a power supply for use in emergency in some cases. The lead acid battery used for such a purpose is called a stationary lead acid battery. It is connected in parallel with a commercial power supply to a load and usually is charged by a small current from the commercial power supply to maintain the capacity of the lead acid storage in 100% state, which is called a float charging. When an irregular condition such as a power outage occurs in the commercial power supply, electric power is supplied to the load from the lead acid battery instead of the commercial power supply.

As such a stationary lead acid battery, a large number of lead acid batteries are connected in series for use. Since such a lead acid battery is subjected to the float charging all the time, it is known that the lead acid battery is gradually degraded and leads to a state in which it cannot supply sufficient power to the load in the end. Thus, to keep track of whether or not sufficient power can be supplied when the commercial power supply falls into an irregular condition, namely, whether or not the capacity of the lead acid battery (residual capacity) is a predetermined amount, the following methods are adopted:

(1) monitoring change in the battery voltage of the lead acid battery and estimating the residual capacity based on the change;
(2) discharging the lead acid battery and estimating the residual capacity;
(3) quickly discharging the lead acid battery for a short time and estimating the residual capacity from the lowering degree of the voltage; and
(4) estimating the residual capacity of the lead acid storage from the value of internal resistance because the internal resistance rises gradually as the lead acid storage is degraded.

According to any of these methods, the state of the lead acid storage is monitored and when the residual capacity reaches a predetermined value or less, the lead acid battery is determined to be at the end of its lifetime and is replaced with a new one.

However, the above methods involve the following problems.

According to the method (1), there are voltage variations caused by the battery proper difference and to connect a large number of lead acid batteries in series for use, the variations are added and thus become large and the method lacks precision and a sufficient margin must be provided for monitoring on practical use.

The method (2) is precise, but a unit for discharging must be installed and when an anomaly occurs in the commercial power supply during the discharging time period, it becomes impossible to deal with the anomaly.

In the method (3), a discharging unit must also be installed. The method (4) is suitable because the error in the measured results is relatively small and does not require a discharging unit, but long-term use of the lead acid battery is desired and more precise state monitoring is desired.

So-called AC four-terminal method is known as a measurement method of the internal impedance of respective lead acid batteries connected in series as a lead acid battery unit.

The AC four-terminal method is a technique of making an AC current flow into the lead acid battery whose internal impedance is to be measured and measuring the electromotive force occurring at the time, thereby finding the internal impedance of the lead acid battery.

FIG. 13 shows a principle of the internal impedance measurement of a lead acid battery by the AC four-terminal method. In this figure, numeral 11 denotes a lead acid battery, numeral 12 denotes a lead acid battery unit, numeral 13 denotes an AC current supplier, and numeral 14 denotes an AC voltage instrument. The AC current supplier 13 and the AC voltage instrument 14 are connected in parallel with the lead acid battery 11.

The lead acid battery unit 12 comprises a plurality of lead acid batteries 11 connected in series to provide the objective voltage value. For example, the electromotive force of each lead acid battery is about 2 V. Six such lead acid batteries are connected in series to provide an electromotive force of about 12 V, which is defined as the lead acid battery unit 12 in the specification.

The AC current supplier 13 supplies an AC current to measure the internal impedance of the lead acid battery 11 (referred to as measurement current in the specification). An AC constant current source serves as the AC current supplier 13, for example, and the internal impedance thereof is infinite on principle.

The AC voltage instrument 14 measures the electromotive force occurring in the lead acid battery 11 by the current supplied by the AC current supplier 13. An AC voltmeter serves as The AC voltage instrument 14, for example, and the internal impedance thereof is infinite on principle.

It is known that the internal impedance of a lead acid battery changes depending on the temperature of the lead acid battery itself and the operating environment temperature. To solve this problem, the following documents disclose that the measurement result of the internal impedance is corrected based on the temperature of the lead acid battery itself.

Japanese Patent Publication No. 6-194428 (cf. column 9, line 29–column 11, line 1; FIGS. 7–9); and Japanese Patent Publication No. 11-7985 (cf. column 1, line 32–column 2, line 25; FIGS. 1 and 2)

The above documents indicate the concept for correcting the measurement result of the internal impedance based on the temperature of the lead acid battery itself; however, the temperature dependency is also varied in accordance with the internal impedance variation in each lead acid battery. In order to solve the problem, it is insufficient to make only a temperature correction based on a temperature correction as taught by the above documents.

SUMMARY OF THE INVENTION

It is therefore an object of the invention to provide more precise monitoring of the state of a lead acid battery for the long-time use.

It is also an object of the invention to provide a method capable of precisely correcting the measurement result of the internal impedance of a lead acid battery based on temperature.

Internal resistance can be found from a voltage of a stationary lead acid battery in response to an AC current applied to the stationary lead acid battery undergoing a float charging with a small charge current. The internal impedance changes with the change in the charged state of the lead acid battery, namely, the residual capacity. That is, the internal impedance increases with lowering of the residual capacity. Therefore, the internal impedance of the lead acid battery is measured, whereby the residual capacity of the lead acid battery can be monitored.

However, the relationship between the internal impedance and the residual capacity of a lead acid battery having a predetermined nominal capacity was first actually examined. A predetermined residual capacity, for example, the point in time at which the capacity lowers to 80% of the nominal capacity was assumed to be the end of the lifetime that the lead acid battery is capable of providing power for a load. An internal impedance at the end of the lifetime of the battery was specified based on the actually examined relationship between the internal impedance and the residual capacity.

When a plurality of batteries, each of which indicates the specified internal impedance, were actually discharged to examine actual residual capacities thereof, it was found that some lead acid batteries do not yet reach 80% and some fall largely below 80%. It was found that the difference reached one year in terms of time period in an extreme case.

Additionally, when the relationship between the internal impedance and the residual capacity of the lead acid battery was actually examined, it was found that clear correlation was not observed in the initial state in which the internal impedance value was low, and that clearer correlation was observed as the internal impedance rose to some extent.

Then, when the data in the state in which the internal impedance value was low was deleted and an approximate expression was found from the correlation after the internal impedance became a given value or more, a high correlation was obtained. It was acknowledged that there is no problem on practical use if the residual capacity was 100% in the time period over which the internal impedance value was low.

The stationary lead acid battery supplies electric power to the load when the commercial power supply is in trouble, and thus requires the residual capacity enabling sufficient electric energy to be supplied to the load. If the stationary lead acid battery falls below the required residual capacity, it needs to be replaced with a new one assuming that the battery reaches the end of the lifetime. In this case, simply by monitoring the state of the lead acid battery as the internal impedance is measured, when the lead acid battery will reach the end of the lifetime cannot be predicted although the time at which the lead acid battery reaches the end of the lifetime can be checked; hitherto, the time has been predicted based on experience.

Then, to predict the end of the lifetime of the lead acid battery in the last stage of the lifetime thereof, the inventors prepared a new approximate expression based on the internal impedance in a past fixed time period from the measurement time and predicted the time at which the lead acid battery would reach the end of the lifetime based on the approximate expression.

Further, the inventors found out that the above-mentioned errors can be lessened by observing the changing rate of the internal impedance, namely, how much is the internal impedance value changed in comparison with the immediately preceding internal impedance value.

In order to eliminate the affection to the measurement value of the internal impedance due to noise from the power supply for the float charging or change in the float charging, the inventors found out that an average value of internal impedance on a weekly or monthly basis needs to be found and the changing rate needs to be observed based on the average value.

FIG. 14 shows the examination result of the average internal impedance measurement values, changing rates, and residual capacities for sixth months using a plurality of sealed lead acid batteries in the last stage of lifetime thereof.

In the table, the internal impedance value was shown as a relative value with the initially designed internal impedance value of a lead acid battery known empirically as 100. It was acknowledged that the residual capacity became 80% or less when the changing rate was 110% or more. The reason why the residual capacity exceeds 100% is that it is described as the ratio to the nominal capacity and usually the real capacity is designed larger than the nominal capacity for manufacturing batteries.

Therefore, the inventors stored the average values of the internal impedance in one time period in time series, found an approximate expression indicating the relationship between the average value of the internal impedance and the one time period, based on the variation with time, predicted the time at which the changing rate of the internal impedance would become a predetermined value or more according to the approximate expression, and displayed the predicted time as the replacement time of the lead acid battery.

Specifically, FIG. 5 shows the variation with time, of the average value of the internal impedance of a sealed lead acid battery every six months until the eighth year after the sixth year. The vertical axis represents the average value of the internal impedance for sixth months and the horizontal axis represents the number of years elapsed since starting the use of the lead acid battery. The average value of the internal impedance was represented as a relative value with the initially designed internal impedance value of the lead acid battery as 100. A cubic function expression of expression (1) was obtained as an expression most approximated to the plotted points.

$$y=2.667x^3-50.857x^2+327.33x-604.17 \tag{1}$$

x denotes the number of years elapsed since starting the use of the lead acid battery and y represents the average value of the internal impedance. As a result of an experiment, it was acknowledged that preferably the approximate expression was a quadratic to quartic function expression.

Letting the time at which the changing rate exceeds 110% per six months, namely, the replacement time be "a" and the value before sixth months be (a−0.5) based on the approximate expression, a and (a−0.5) are assigned to x to find expressions. Then, the following expressions (2) and (3) are obtained:

$$ya=2.667a^3-50.857a^2+322.33a-604.17 \tag{2}$$

$$yb=2.667(a-0.5)^3-50.857(a-0.5)^2+322.33(a-0.5)-604.17 \tag{3}$$

If a that the ratio between the two expressions becomes 1.1, namely, ya/yb=1.1 is found, a=8.17. Therefore, it can be predicted that it is necessary to replace the lead acid battery in 8.17 years after starting use of the battery.

In fact, the lead acid battery maintained the residual capacity of 85% in the eighth year, but the residual capacity was lowered to 76% in 8.5 years after starting use of the lead acid battery, the accuracy of the prediction can be acknowledged.

Specifically, according to the invention, there is provided a method of monitoring a state of a battery, comprising the steps of:

determining a threshold value of an internal impedance of the battery;

preparing an approximate expression indicating a correlation between a residual capacity of the battery and an internal impedance of the battery which is greater than the threshold value;

measuring the internal impedance of the battery;

determining the residual capacity as an initial value when the measured internal impedance is the threshold value or less; and monitoring the residual capacity with the approximate expression when the measured internal impedance is greater than the threshold value.

According to the invention, there is also provided a system of monitoring a state of a battery, comprising:

a storage, in which an approximate expression indicating a correlation of a residual capacity of the battery and an internal impedance of the battery which is greater than a threshold value is previously stored;

an instrument, which measures the internal impedance of the battery; and a monitor, which monitors the residual capacity with the approximate expression when the measured internal impedance is greater than the threshold value, and determines the residual capacity as an initial value when the measured internal impedance is the threshold value or less.

According to the invention, there is also provided a method of monitoring a state of a battery, comprising the steps of;

measuring an internal impedance of the battery every time when a first time period is elapsed;

storing the measured internal impedance as time-serial impedance data;

monitoring a residual capacity of the battery;

gathering the time-serial impedance data during a second time period prior to a time point at which the monitored residual capacity becomes a threshold value or less;

obtaining an approximate expression indicating a correlation between the internal impedance and the residual capacity based on the gathered time-serial impedance data; and predicting a residual lifetime of a battery based on the obtained approximate expression.

Preferably, the threshold value is 85% of an initial capacity.

According to the invention, there is also provided a method of monitoring a state of a battery, comprising the steps of:

measuring an internal impedance of the battery every time when a first time period is elapsed;

storing the measured internal impedance as time-serial impedance data;

obtaining an average value of the time-serial impedance data every time when a second time period is elapsed;

comparing an average value of a certain second time period and a preceding second time period to obtain a changing rate of the average value; and generating an alarm when the obtained changing rate is not less than a predetermined value.

According to the invention, there is also provided a method of monitoring a state of a battery, comprising the steps of:

measuring an internal impedance of the battery every time when a first time period is elapsed;

storing the measured internal impedance as time-serial impedance data;

obtaining an average value of the time-serial impedance data every time when a second time period is elapsed;

obtaining an approximate expression based on the time-serial impedance data every time when the second time period is elapsed;

predicting a time point at which a changing rate of the average value becomes a predetermined value or more, based on the approximate expression; and displaying the predicted time point as a residual lifetime of the battery.

According to the invention, there is also provided a system of monitoring a state of a battery, comprising:

a instrument, which measures an internal impedance of the battery every time when a first time period is elapsed;

a storage, which stores the measured internal impedance as time-serial impedance data;

a monitor, which monitors a residual capacity of the battery; and a calculator, which gathers the time-serial impedance data during a second time period prior to a time point at which the monitored residual capacity becomes a threshold value or less; obtains an approximate expression indicating a correlation between the internal impedance and the residual capacity based on the gathered time-serial impedance data; and predicts a residual lifetime of a battery based on the obtained approximate expression.

Preferably, the threshold value is 85% of an initial capacity.

According to the invention, there is also provided a system of monitoring a state of a battery, comprising:

an instrument, which measures an internal impedance of the battery every time when a first time period is elapsed;

a storage, which stores the measured internal impedance as time-serial impedance data;

a calculator, which obtains an average value of the time-serial impedance data every time when a second time period is elapsed;

a comparator, which compares an average value of a certain second time period and a preceding second time period to obtain a changing rate of the average value; and an alarm, which generates an alarm when the obtained changing rate is not less than a predetermined value.

According to the invention, there is also provided a system of monitoring a state of a battery, comprising:

an instrument, which measures an internal impedance of the battery every time when a first time period is elapsed;

a storage, which stores the measured internal impedance as time-serial impedance data;

a calculator, which obtains an average value of the time-serial impedance data every time when a second time period is elapsed; obtains an approximate expression based on the time-serial impedance data every time when the second time period is elapsed; and predicts a time point at which a changing rate of the average value becomes a predetermined value or more, based on the approximate expression; and a display, which displays the predicted time point as a residual lifetime of the battery.

According to the invention, there is also provided a method of measuring an internal impedance of a battery, comprising the steps of:

measuring an internal impedance and a temperature of the battery at the same time;

storing the measured internal impedance and the measured temperature as time-serial impedance data and time-serial temperature data;

obtaining a correction coefficient based on a correlation between the time-serial impedance data and the time-serial temperature data during a predetermined time period; and correcting the measured internal impedance with the correction coefficient as a value at a reference temperature.

According to the invention, there is also provided a system for measuring an internal impedance of a battery, comprising:

an instrument, which measures an internal impedance and a temperature of the battery at the same time;

a storage, which stores the measured internal impedance and the measured temperature as time-serial impedance data and time-serial temperature data;

a calculator, which obtains a correction coefficient based on a correlation between the time-serial impedance data and the time-serial temperature data during a predetermined time period; and a corrector, which corrects the measured internal impedance with the correction coefficient as a value at a reference temperature.

BRIEF DESCRIPTION OF THE DRAWINGS

The above objects and advantages of the present invention will become more apparent by describing in detail preferred exemplary embodiments thereof with reference to the accompanying drawings, wherein:

FIG. 14 is a table showing actual examined results of the internal impedance, the changing rate of the internal impedance and the residual capacity of lead acid batteries.

DETAILED DESCRIPTION OF THE PREFERRED EMBODIMENTS

Figure 1:
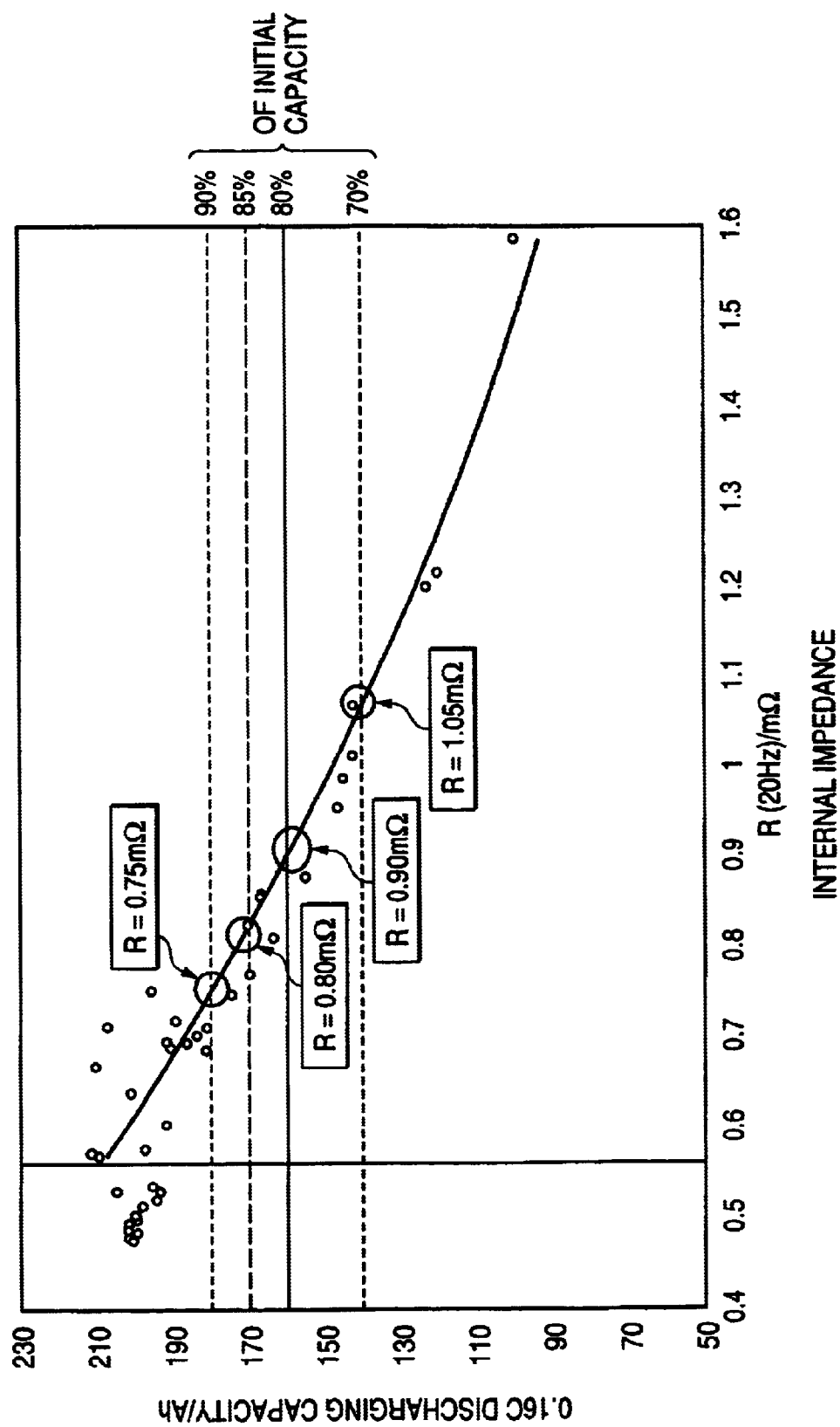
FIG. 1 is a drawing to show the relationship between the internal impedance and the residual capacity of a lead acid battery.

FIG. 1 shows the progression of the residual capacity and internal impedance of a fully charged, sealed lead acid battery having a nominal capacity of 200 Ah by conducting an acceleration lifetime test. The horizontal axis indicates the internal impedance of the lead acid battery and the vertical axis indicates the discharge capacity when the lead acid battery was discharged with a current of 0.16 C. As the conditions of the acceleration lifetime test, the lead acid battery was entered in a water tank at 65° C. and a small current of 1 A was continuously made to flow thereinto. An AC current of a constant frequency of 20 Hz was applied and the internal impedance was calculated based on the response voltage and the phase difference at the time.

The data indicating initial small values of the internal impedance values obtained in the initial stage of lifetime of the battery (in the example, the portion of 0.568 mΩ and less) was omitted, and an approximate curve of the correlation between the internal impedance and the residual capacity was found based on the internal impedance values larger than the initial small values. As a result, the following correlation approximate expression was found.

$$y=314.8e^{-0.7409x}$$

Here, y represents a residual capacity and x represents an internal impedance. The correlation coefficient became 0.953; high correlation was obtained as compared with the case where the initial internal impedance was also included in the calculation. The internal impedance is a value corrected based on the temperature. When the correlation coefficient is 1.00, it means that there is no deviation from the actual relation; as the correlation coefficient deviates from 1.00, it means that the deviation is larger.

Next, the approximate expression was input to a storage of a computer. The computer was connected to the above-mentioned sealed lead acid battery having a nominal capacity of 200 Ah, AC current input lines were connected to positive and negative terminals of each lead acid battery, and floating charging was continued with a current of 1 A. The values of the response voltage when AC current of 20 Hz was applied to the lead acid battery, the applied AC current, and the like were input to a calculator once a day. The calculator performed calculations to find the internal impedance, and calculated the residual capacity of the battery based on the approximate expression previously stored in the storage. The residual capacity is displayed, so that the state of each lead acid battery was able to be monitored, It was acknowledged that there was not much difference between the display value and the result of a residual capacity test of examining the lead acid battery as it was actually discharged with discharge current of 0.16 C., and that it was possible to use practically.

Figure 2:
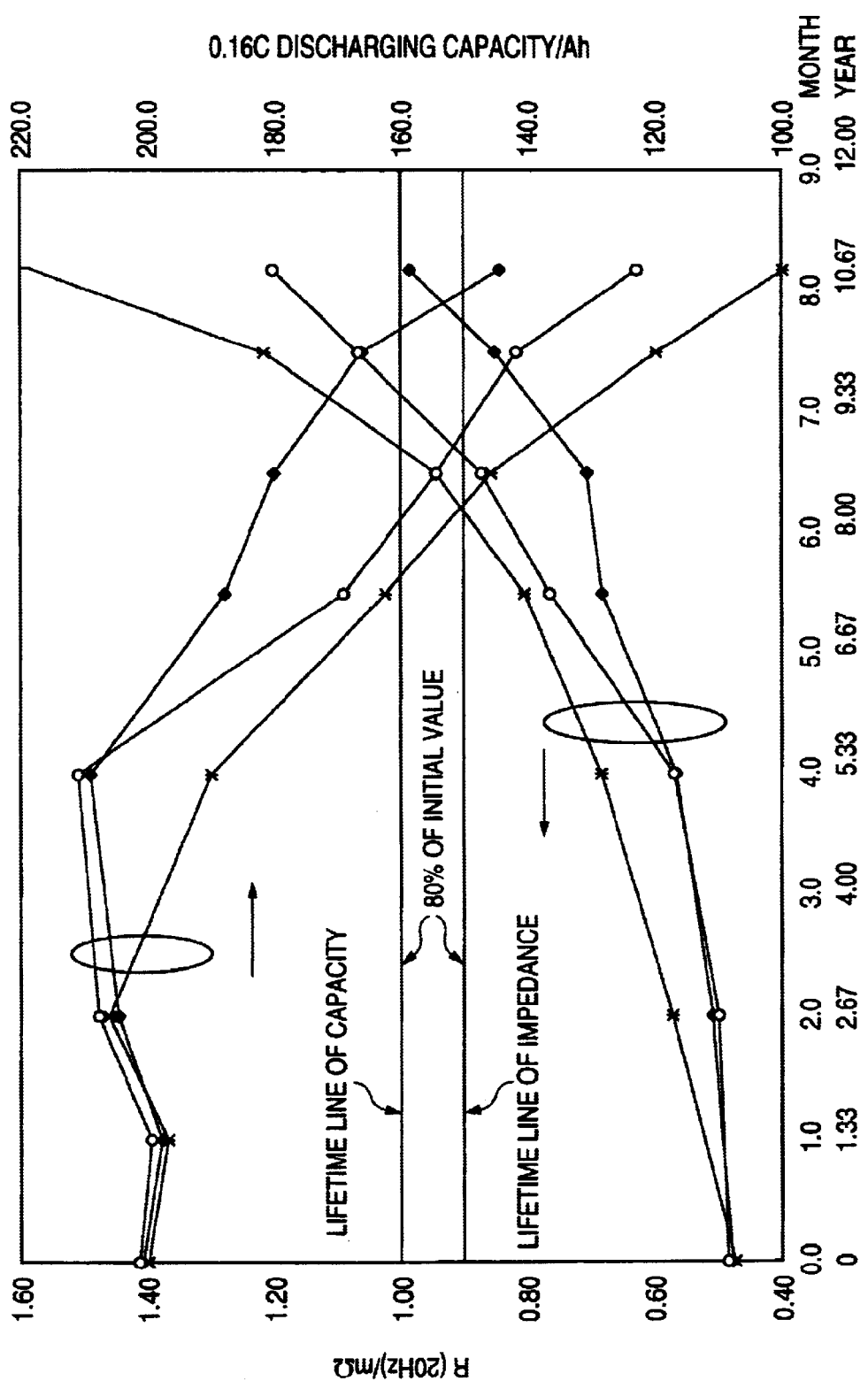
FIG. 2 is a drawing to show the relationship among time period, internal impedance, and lead acid battery capacity.

Next, a prediction method of the lifetime of a lead acid battery will be discussed. The lifetime of the above battery was assumed to be the time at which the residual capacity reached 80% of the initial value FIG. 2 shows the progression of the internal impedance (R) and the residual capacity of each of three batteries placed at different locations by applying an AC current of 20 Hz to each of lead acid batteries when 12 lead acid batteries in the first example are arranged close to each other and are connected in series and are subjected to float charging with a current of 1 A. The horizontal axis indicates the number of months of the acceleration lifetime test in the first example (the predicted number of years is also indicated below the number of months), and the vertical axis indicates the internal impedance (R) and the residual capacity of each lead acid battery at the left and right. It is seen that the lead acid batteries show the different progression of the internal impedance values. It seems that the different progression is caused by the environment of the lead acid battery depending on the location, particularly, the effect of the temperature of the lead acid battery caused by the location during the float charging.

It is obvious from the result that if the time at which the residual capacity will reach 80% of the initial value is predicted simply from the internal impedance value, it differs from the actual time. That is, the behavior of each lead acid battery varies depending on the environment in which the lead acid battery is installed, etc., in such a manner that the internal impedance of one lead acid battery rises early and the residual capacity reaches the lifetime relatively early, and that one lead acid battery rises rapidly and later rises slowly. Then, when the residual capacity is 85% in the proximity of the end of the lifetime (in the example, at least one year before the lifetime ends), in the later state of the lead acid battery is predicted from the progression of the internal impedance in the preceding six months, and later this prediction is updated based on the data in six months before the data collection time. Accordingly, it is made possible to predict the lifetime more precisely.

Figure 3:
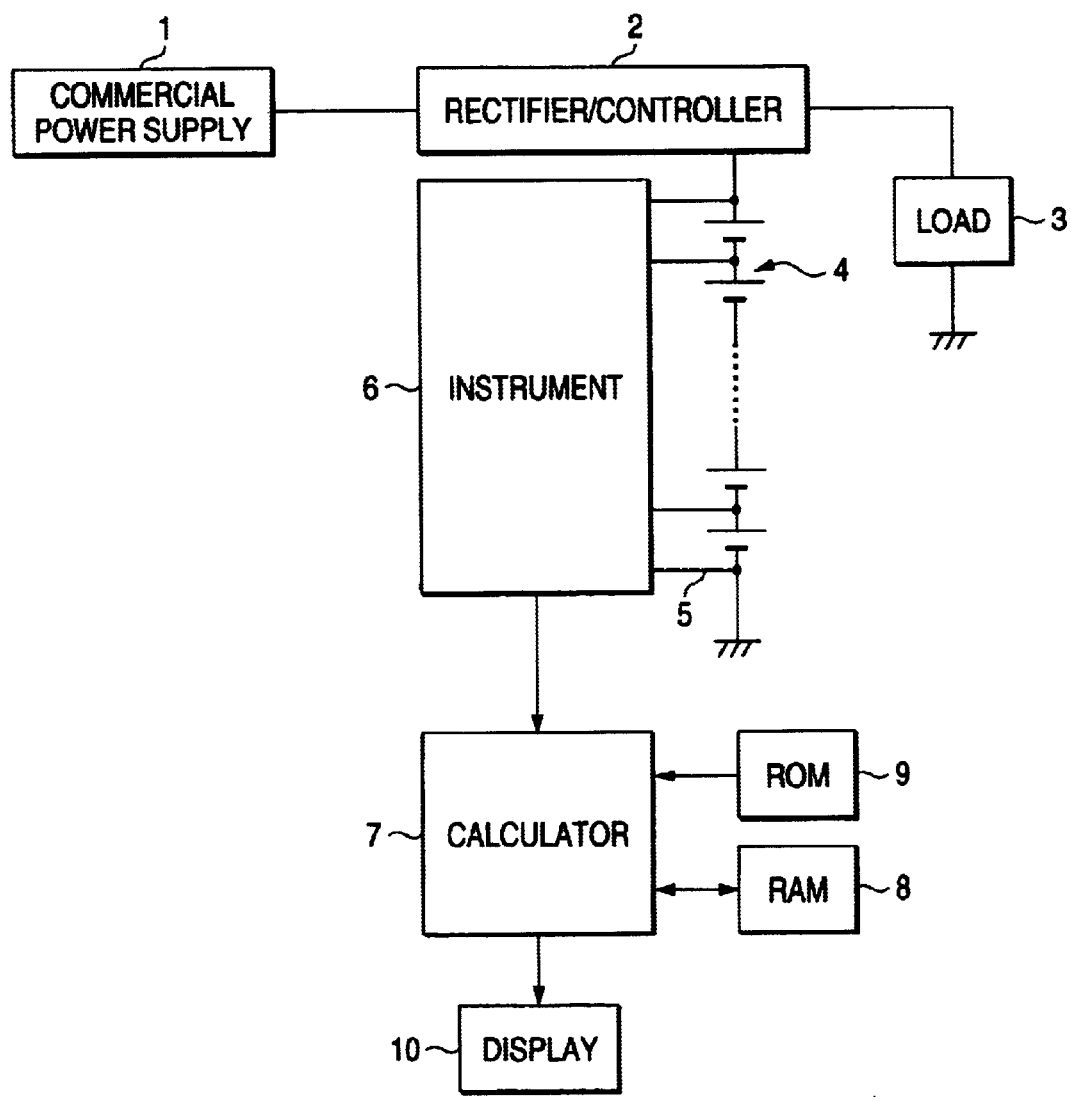
FIG. 3 is a schematic representation of a monitoring system according to a first embodiment of the invention.

Specifically, as shown in FIG. 3, a commercial power supply 1 is connected to a load 3 through a rectifier/controller 2 and a lead acid battery 4 is connected in parallel with the load 3. The lead acid battery 4 comprises 12 fully charged, sealed lead acid batteries each having a nominal capacity of 200 Ah connected in series. AC current application lines 5 are connected to positive and negative terminals of each lead acid battery and a float charging current of 1 A is made continuously to flow into the lead acid batteries 4 connected in series. An AC current of 20 Hz is applied from an instrument 6 to each lead acid battery 4 over the application lines 5 once a day with a timer.

Information of response voltage and phase difference is input to a calculator 7 and the measurement date and the internal impedance are stored in a RAM 8. The temperature of each lead acid battery is measured with a thermistor (not shown) fixed to the battery container side of the lead acid battery and is input to the calculator 7. The measured internal impedance value is corrected based on the temperature according to the calibration curve indicating the correlation between temperature and internal impedance which is previously stored in the RAM 8. The residual capacity of the lead acid battery is found by a program stored in a ROM 9 according to an approximate expression indicating the correlation between the internal impedance and the residual capacity which is previously stored in the RAM 8.

The calculator 7 stores the result in the RAM 8 as data and a message "GOOD" is displayed on a display 10 until the residual capacity lowered to 85% of the initial capacity and a message "WARNING" is displayed in the range of 85% to 80%. While displaying the message "WARNING", the calculator 7 finds an approximate expression of quadratic function, aside from the above-mentioned approximate expression, based on the internal impedance values in the six months prior to the time point, to calculate the time at which the residual capacity of the lifetime would become 80%, and display the predicted residual lifetime on the display 10. The approximate expression is found with the internal impedance values not corrected based on the temperature. Thus, it is made possible to predict the lifetime close to the actual lifetime.

Figure 4:
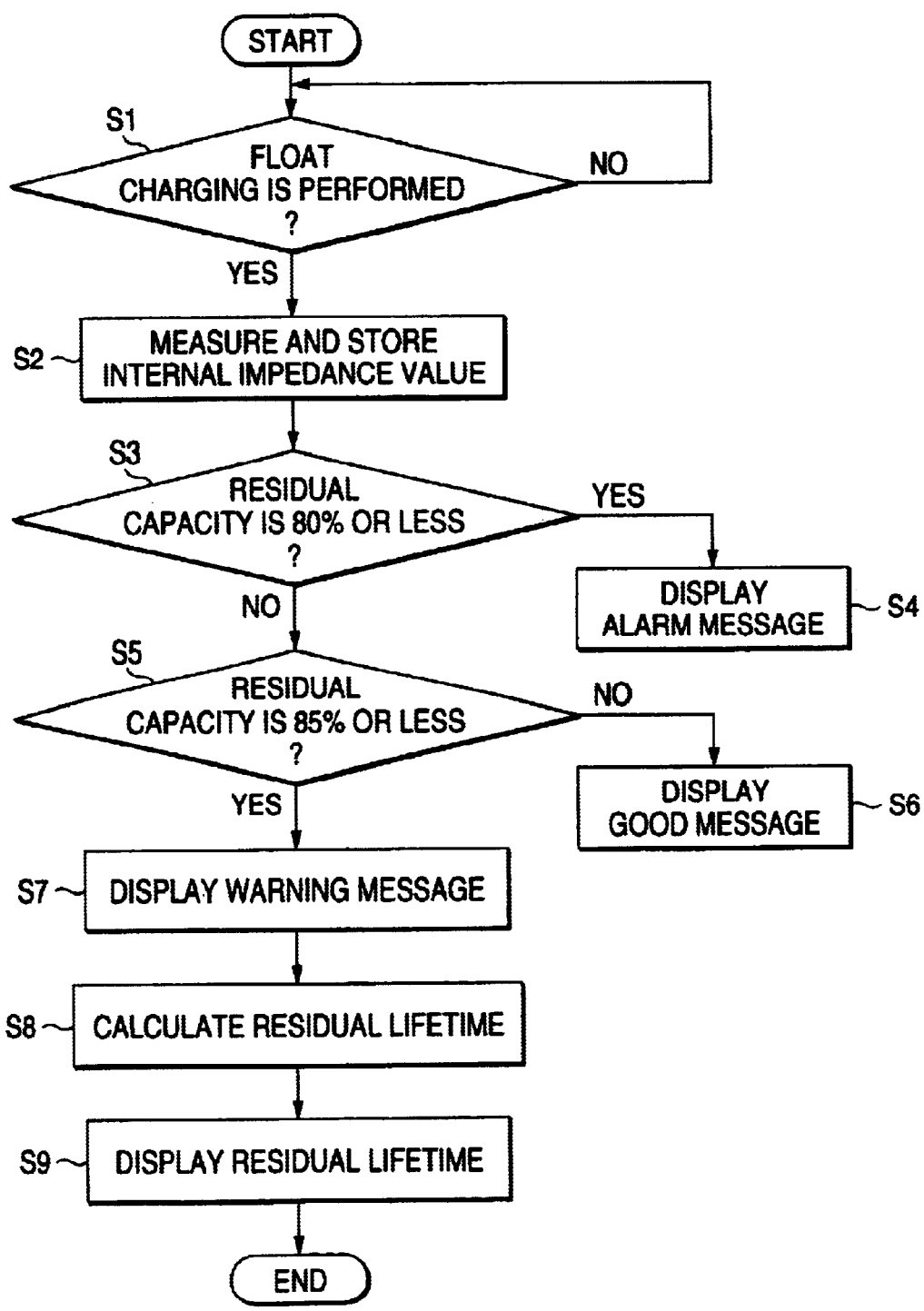
FIG. 4 is a flowchart showing processing performed in the monitoring system of FIG. 3.
Figure 5:
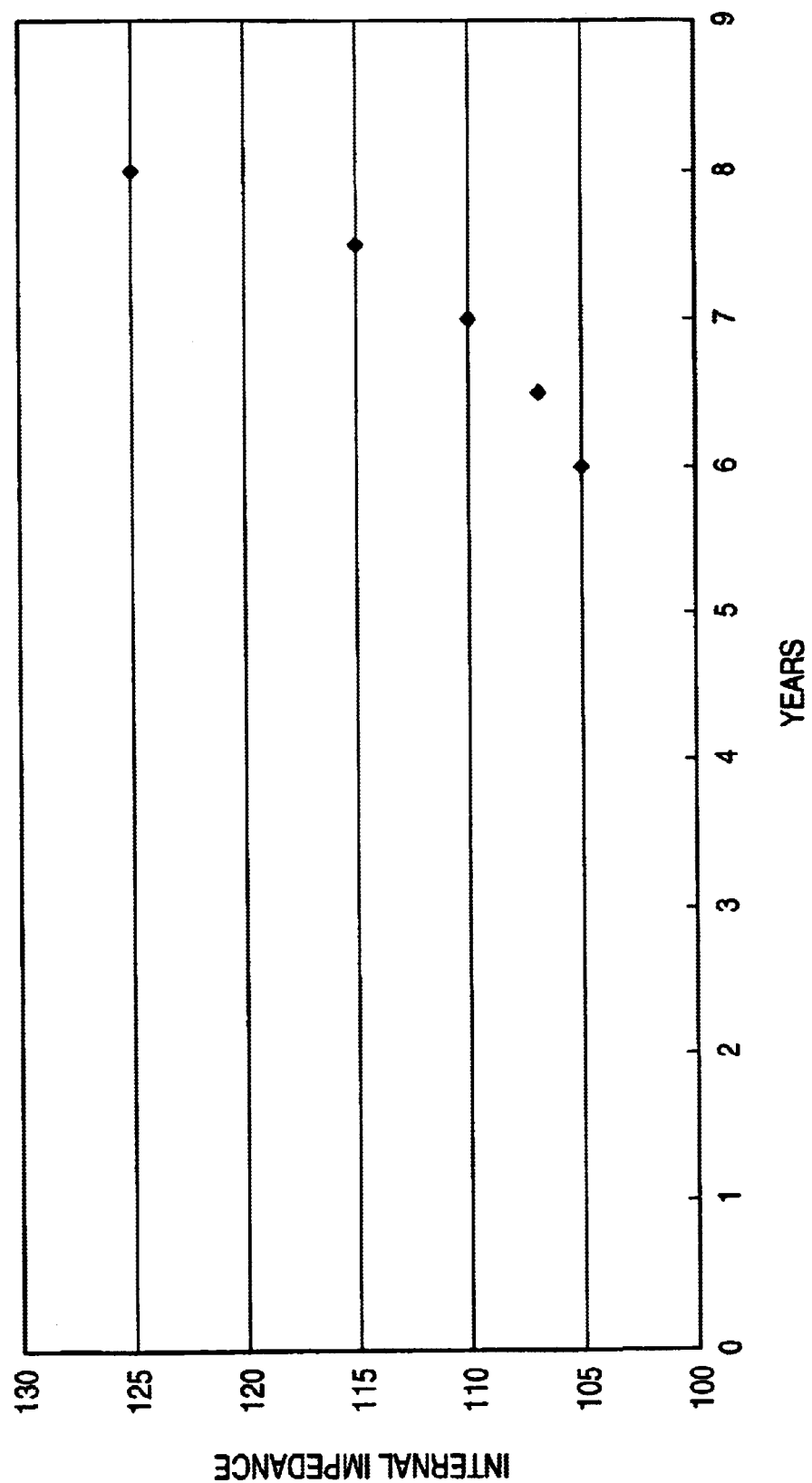
FIG. 5 is a drawing to show the variation with time, of the average value of internal impedance and an approximate curve.

The calculator 7 performs processing shown in FIG. 4 using the program stored in the ROM 9. First, whether or not the lead acid battery is subjected to the float charging is checked (step S1). When an irregular condition such as a power outage occurs in the commercial power supply, the lead acid battery is discharged for supplying electric power to the load. After the commercial power supply is recovered from the irregular condition, the lead acid battery is charged by the commercial power supply. When the lead acid battery is fully charged, again it is subjected to float charging When the lead acid battery is discharged or is charged, no AC current is applied and no internal impedance is measured. To do this, an AC current is periodically applied only when the lead acid battery is in the float charging state. The float charging state was determined by monitoring the voltage of the lead acid battery.

When the lead acid battery is in the float charging state, an AC current is applied, the internal impedance of the lead acid battery is calculated and measured, and the residual capacity is found according to the correlation approximate expression between the internal impedance and the residual capacity, which is previously stored in the RAM 8 (step S2). Next, whether or not the found residual capacity is equal to or greater than 80% of the initial value defined as the lifetime is determined (step S3). If the residual capacity is less than 80%, an alarm message "REPLACE" is displayed (step S4). If the residual capacity is 80% or more, then whether or not the residual capacity is 85% or more is determined (step S5). If the residual capacity is 85% or more, the message "GOOD" is displayed (step S6). If the residual capacity is less than 85%, the message "WARNING" is displayed (step S7), and the correlation between the internal impedance and the residual capacity is found as an approximate expression of quadratic function, from the progression of the internal impedance values in the six months prior to the current time point. The time at which the residual capacity will reach 80% is calculated according to the approximate expression Subtracting the current lifetime from the predicted lifetime, the residual lifetime is found and displayed on the display 10 (step S9). After then, the operations are executed repeatedly.

Table 1 shows the check result of lifetime prediction according to the approximate expression when the residual capacity became 85% and the actually measured lifetime (years) by conducting an acceleration lifetime test with respect to five sealed lead acid batteries placed at different locations. The error between the prediction and the actual measurement was within about 0.2 years; almost satisfactory result was obtained.

TABLE 1

| battery No. | predicted lifetime (years) | measured lifetime (years) |
| --- | --- | --- |
| 1 | 1.6 | 1.4 |
| 2 | 1.4 | 1.2 |
| 3 | 1.2 | 1.4 |
| 4 | 1.5 | 1.3 |
| 5 | 1.7 | 1.6 |

Table 2 shows the examination result of the capacity and the display state of each of five sealed lead acid batteries different in residual capacity. The result was also almost satisfactory.

TABLE 2

| battery No. | residual capacity (Ah) | message | predicted lifetime (years) |
| --- | --- | --- | --- |
| 1 | 195 | GOOD | |
| 2 | 166 | WARNING | 0.8 |
| 3 | 140 | REPLACE | |
| 4 | 200 | GOOD | |
| 5 | 168 | WARNING | 1.2 |

In this embodiment, the internal impedance values at the time when the prediction is conducted are used, however, the average value of internal impedance data in a predetermined time period may be used.

Such a configuration will be discussed as a second embodiment of the invention.

In this embodiment, the calculator 7 averaged the internal impedance values in the past six months stored every six months according to a program stored in ROM 9 to find an average value, and stored the average value in the RAM 8 in time series as the internal impedance average value. The calculator 7 compared the internal impedance average value with that in the immediately preceding six months to find the changing rate. When the changing rate exceeded 110%, the calculator 7 displayed an alarm message "REPLACE" on the display 10. Any other things are the same as the first embodiment and the detailed explanation will be omitted.

Figure 6:
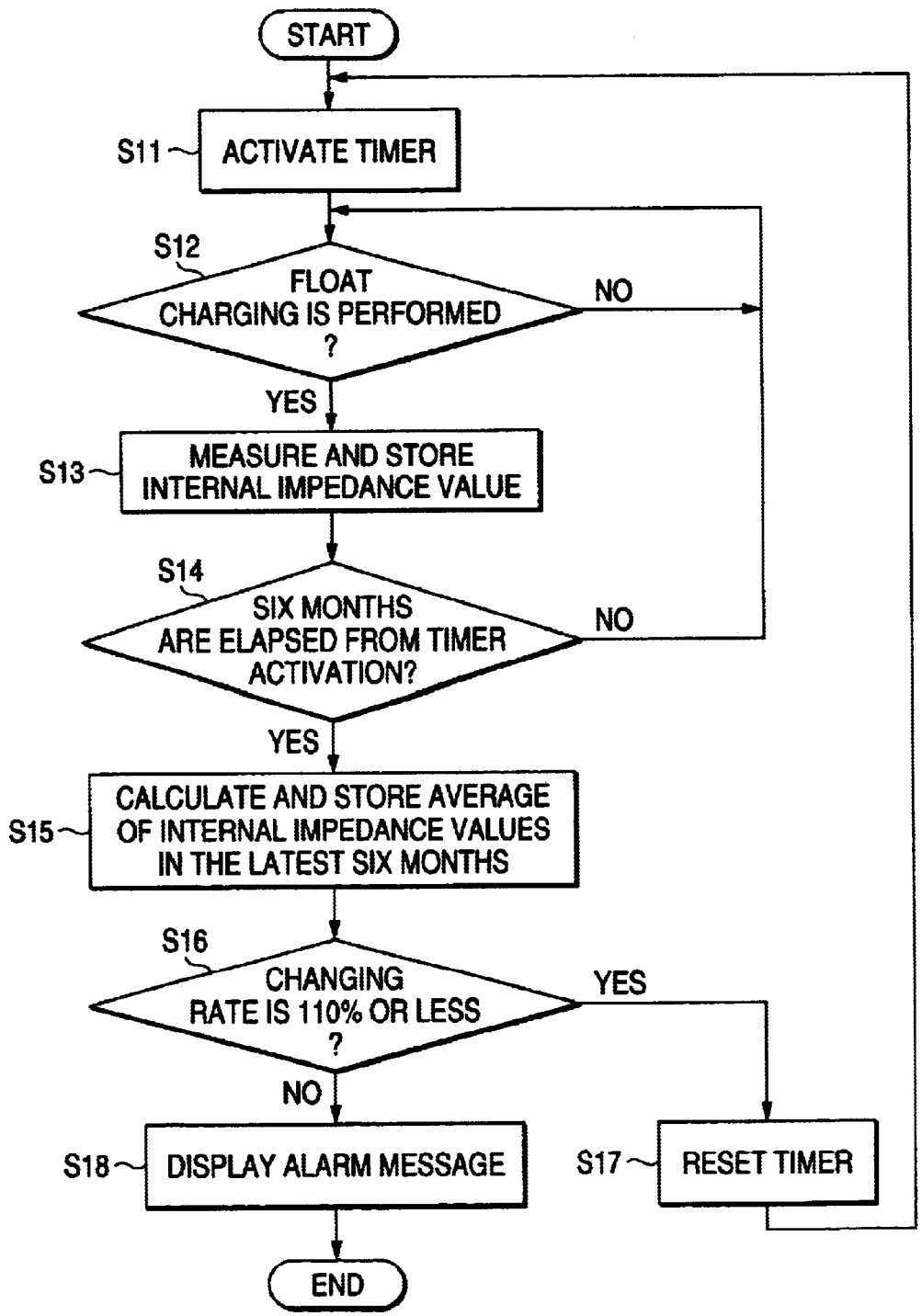
FIG. 6 is a flowchart showing processing performed in a monitoring system according to a second embodiment of the invention.

The calculator 7 performs processing according shown in FIG. 6 using the program stored in the ROM 9. First, the timer is started (step S11) and whether or not the lead acid battery is subjected to the float charging is checked (step S12). When an irregular condition such as a power outage occurs in the commercial power supply, the lead acid battery is discharged for supplying electric power to the load. After the commercial power supply is recovered from the irregular condition, the lead acid battery is charged by the commercial power supply. When the lead acid battery is fully charged, again it is subjected to the float charging. When the lead acid battery is discharged or is charged, no AC current is applied and no internal impedance is measured. To do this, an AC current is periodically applied only when the lead acid battery undergoes float charging. The float charging state was determined by monitoring the voltage of the lead acid battery.

The internal impedance is measured based on the applied AC current and the response voltage at the time and is stored in the RAM 8 (step S13). Next, whether or not the time of six months has elapsed is determined using the timer (step S14). If the time of six months has not yet elapsed, preparation is made for the next internal impedance measurement. If the time of six months has elapsed, the internal impedance values in six months stored so far are calculated to find an average value and the average value is stored in the RAM 8 (step S15). The average value of the internal impedance found this time is compared with the previously found average value to calculate the changing rate (step S16). If the changing rate is 110% or less, the timer is reset (step S17) and to record the internal impedance values in the next six months, the timer is again started. In this case, the previous data was left and new data was stored as data in the next six months without overwriting the previous data with the new data. At the time, the data was stored together with age-based data in the first half-year and that in the first year.

If the changing rate exceeds 110%, the alarm message is displayed (step S18) and the program is terminated. The message display is continued.

The apparatus was actually used, the sealed lead acid battery 4 was placed in an atmosphere of temperature 65° C., and the lead acid battery after being fully charged is continuously subjected to a float charging with a small current of 1 A to conduct an acceleration lifetime test. An AC current of a constant frequency of 20 Hz was applied once a day by the internal impedance instrument 6, the internal impedance was calculated based on the response voltage at the time, the average value of the internal impedance in six months was found every half-month, and the state was monitored. As a result, the alarm message was displayed in about six months. When the lead acid battery was actually discharged and the residual capacity was examined, the residual capacity was not greater than 80% of the initial capacity.

Figure 7:
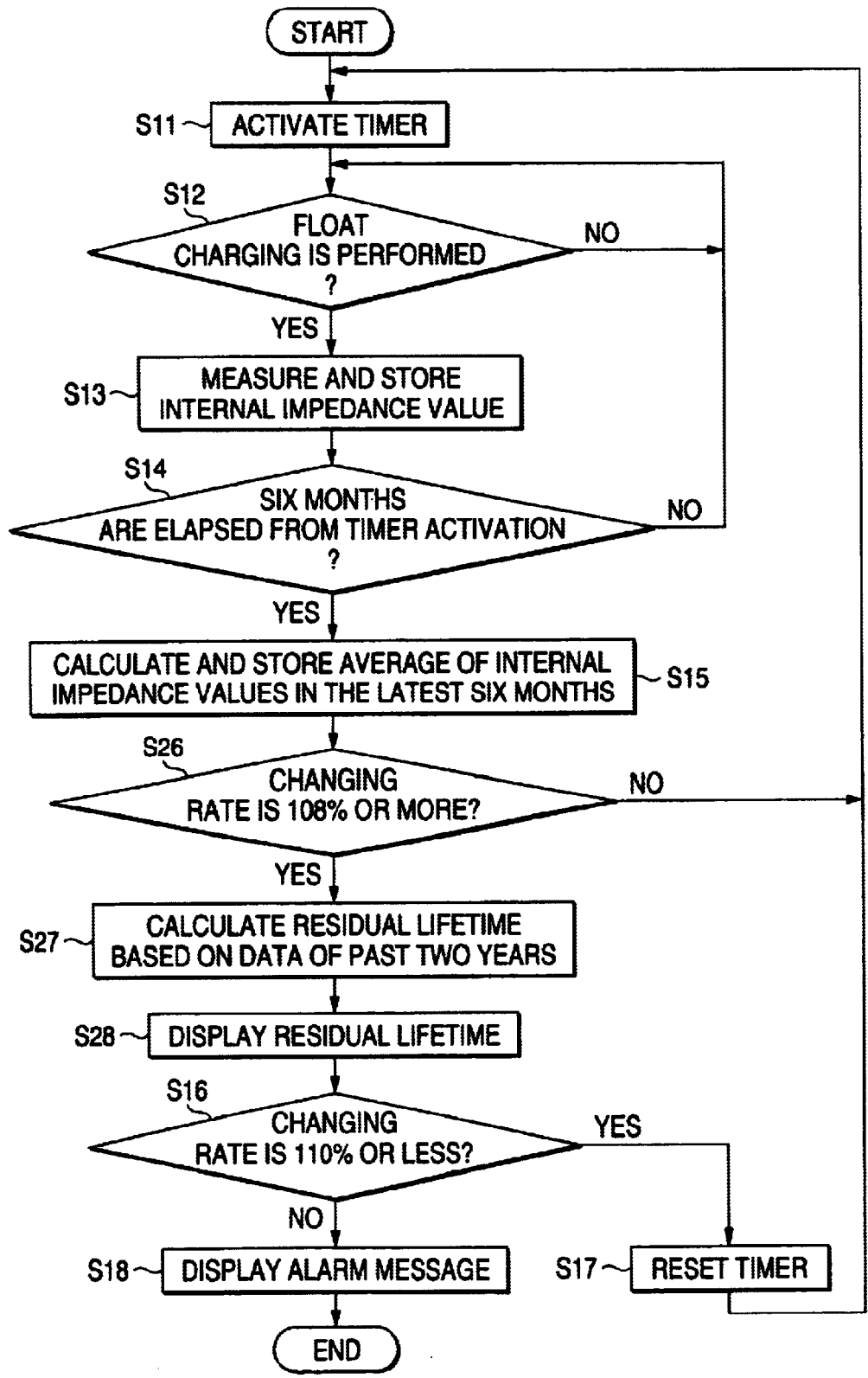
FIG. 7 is a flowchart showing processing performed in a monitoring system according to a third embodiment of the invention.

There will be discussed a third embodiment of the invention in which the residual lifetime is predicted based on the progression of changing rates. The same apparatus previously described with reference to the first and second embodiments is used, but the calculator 7 executes a different program from that in the above embodiments. FIG. 7 is a flowchart executed by the program stored in the ROM 9. The steps S11 through S15 are identical with those of the second embodiment. After that, whether or not the changing rate is 108% or more is determined (step S26). If the changing rate is less than 108%, preparation is made for the next internal impedance measurement. If the changing rate is 108% or more, the relationship between the average value of the internal impedance and the time is calculated from the data in the past two years, namely, change in the average values of the internal impedance in time series and the variation with time, and an approximate expression of cubic function is found. Based on this, the time at which the changing rate of the average values of the internal impedance will exceed 110% is calculated (step S27) and is displayed on the display 10 as the residual lifetime, namely, the replacement time of the lead acid battery (step S28).

The execution result of the previously shown lifetime acceleration test was almost satisfactory.

In the embodiments, the internal impedance measurement is mainly described. A battery voltage measurement system can be added so the state of the lead acid battery can be monitored at the same time.

Figure 8:
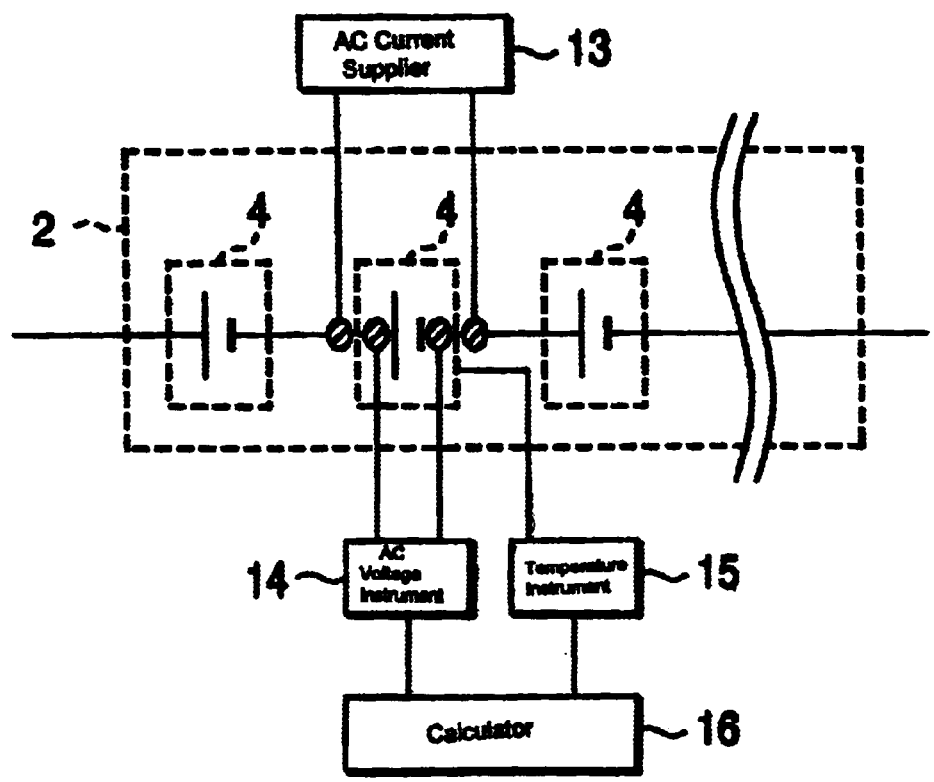
FIG. 8 is a diagram showing an example of an internal impedance instrument according to the invention.
Figure 13:
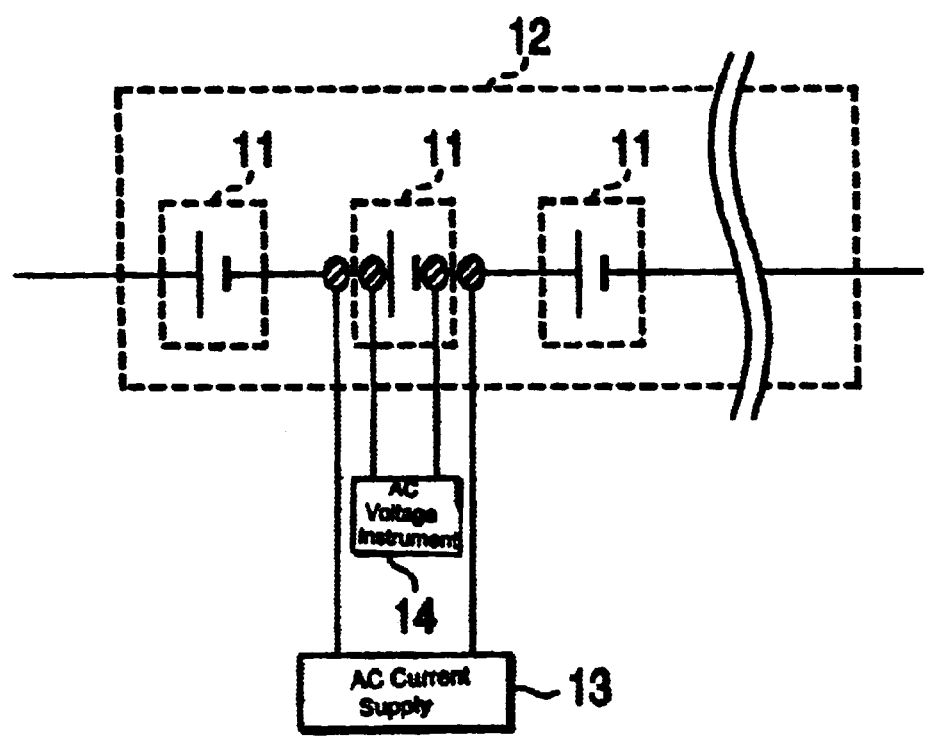
FIG. 13 is a diagram showing the principle of internal impedance measurement of a lead acid battery by an AC four-terminal method.

FIG. 8 schematically shows an example of an internal impedance instrument for a lead acid battery. In this figure, numeral 4 denotes a lead acid battery, numeral 12 denotes a lead acid battery unit, numeral 13 denotes an AC current supplier, and numeral 14 denotes an AC voltage instrument. The AC current supplier 3 and the AC voltage instrument 4 are connected in parallel with the lead acid battery 4 as well as the configuration shown in FIG. 13. Further, in FIG. 8, numeral 15 denotes a temperature instrument for measuring the temperature of the lead acid battery 4 and numeral 16 denotes a calculator for processing signals sent from the AC voltage instrument 4 and the temperature instrument 5.

A lead-acid battery, etc., is used as each of the lead acid batteries 4 making up the lead acid battery unit 12. It is effective to apply the invention to a sealed lead-acid battery hard to determine degradation based on visual confirmation of the liquid level, etc.

The lead acid battery unit 12 comprises a plurality of lead acid batteries 4 connected in series to provide the objective voltage value. If the lead acid battery 4 is a lead-acid battery having an electromotive force of about 2 V, six, 12, and 24 lead-acid batteries can be connected in series to provide electromotive forces of about 12 V, about 24 V, and about 48 V, respectively.

The AC current supplier 13 supplies an AC current to measure the internal impedance of the lead acid battery 4 and serves as an AC constant current source. The AC current supplier 13 may supply an AC current to the lead acid battery 4 or may cause an AC current to be discharged from the lead acid battery 4.

It is desirable that the waveform of the AC current supplied from the AC current supplier 13 should be substantially a sine wave from the viewpoint of measuring the internal impedance of the lead acid battery 4 without receiving the effect of a harmonic component.

The AC voltage instrument 14 measures the electromotive force occurring in the lead acid battery 4 by the current generated by the AC current supplier 13.

The temperature instrument 15 measures the temperature of the lead acid battery 4 and is implemented as a temperature sensor, etc., for example.

The calculator 16 has a function of calculating the internal impedance data of the lead acid battery 4 from the relationship between the current value generated by the AC current supplier 13 and the measured electromotive force occurring in the lead acid battery 4 by the current supplied by the AC current supplier 13. The calculator 16 further has a function of correcting the internal impedance data of the lead acid battery 4 based on the temperature data of the lead acid battery 4 measured by the temperature instrument 15.

The calculator 16 finds a temperature correction coefficient from the correlation between the internal impedance data of the lead acid battery 4 and the temperature data in a given time period and corrects the internal impedance data of the lead acid battery 4, so that the error at the temperature correction time can be lessened and the measurement result of the internal impedance data of the lead acid battery can be precisely corrected based on the temperature.

Next, how to measure the internal impedance of a lead acid battery will be discussed with measurement data illustrated.

Figure 9:
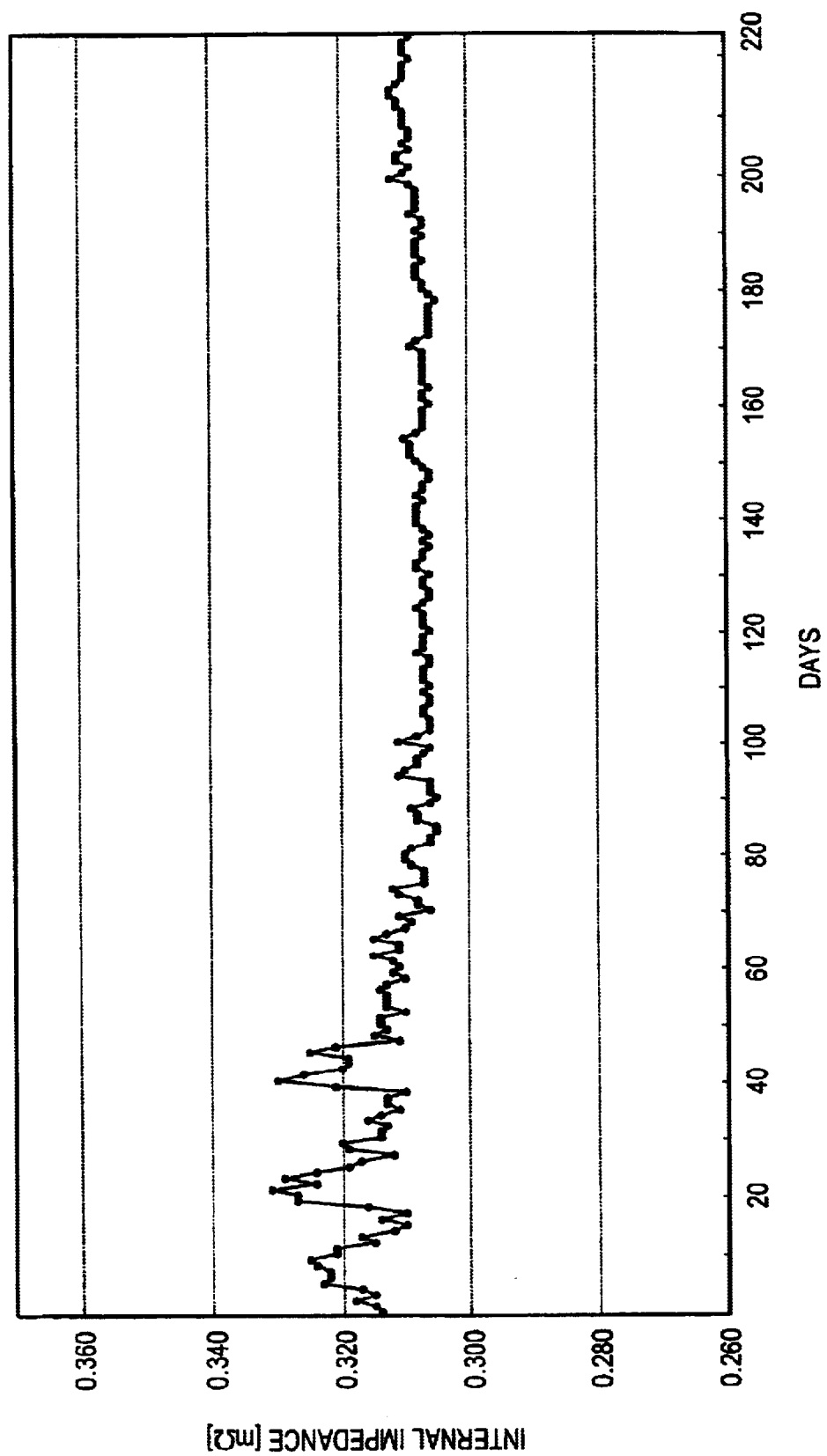
FIGS. 9 and 10 are graphs showing examples of the measurement result of the internal impedance of a lead acid battery.

FIG. 9 is a graph to show an example of the measurement result of internal impedance. It shows the result of measuring the internal impedance of a specific lead acid battery once a day during 220 days.

Figure 10:
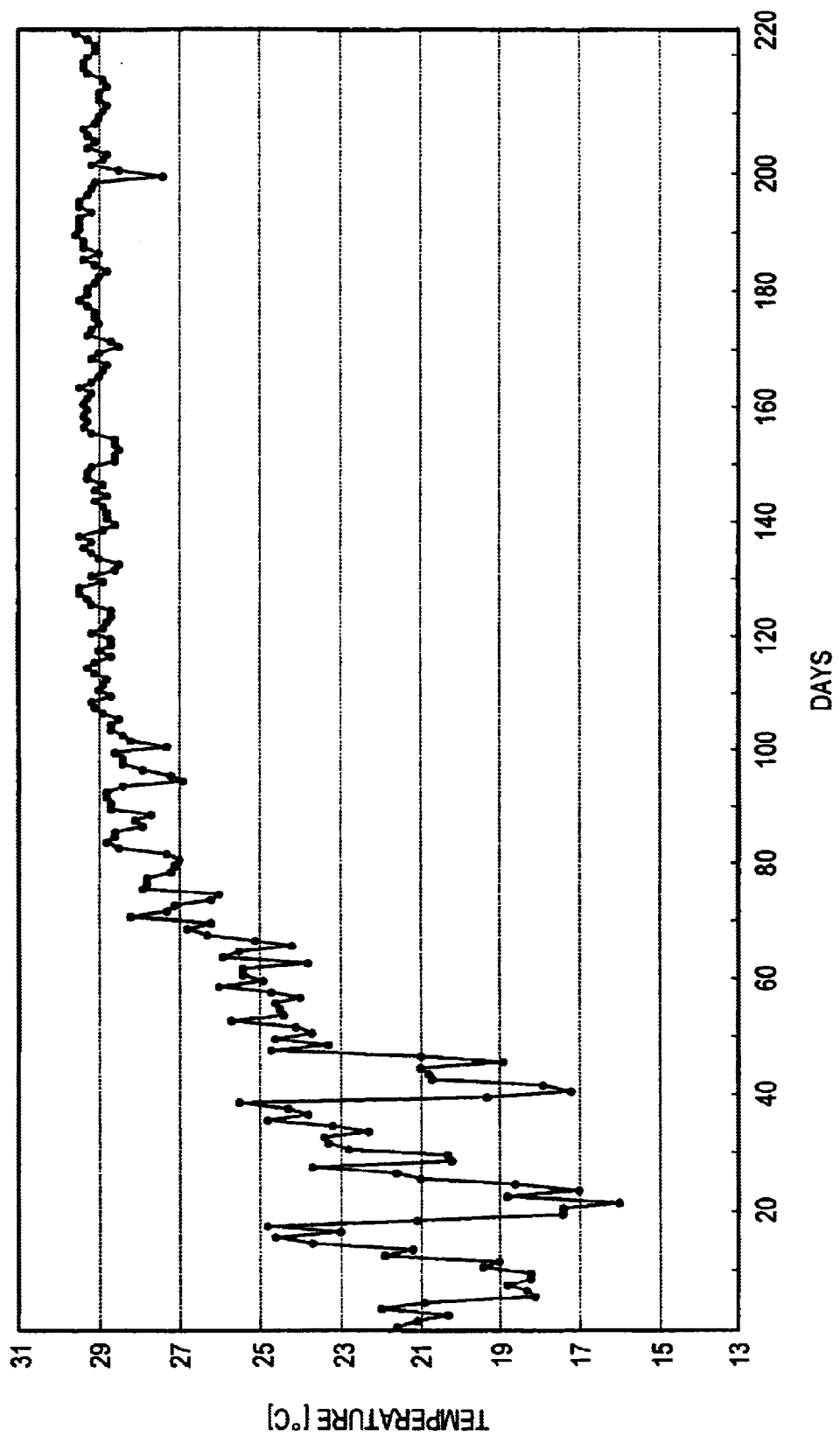

Next, the result of temperature measurement conducted at the same time as the measurement of the internal impedance of the lead acid battery 4 is shown. FIG. 10 is a graph to show an example of the measurement result of the temperature of the lead acid battery. Making a comparison between FIGS. 9 and 10, it is seen that as the temperature of the lead acid battery 4 lowers, the internal impedance of the lead acid battery 4 tends to rise.

Figure 11:
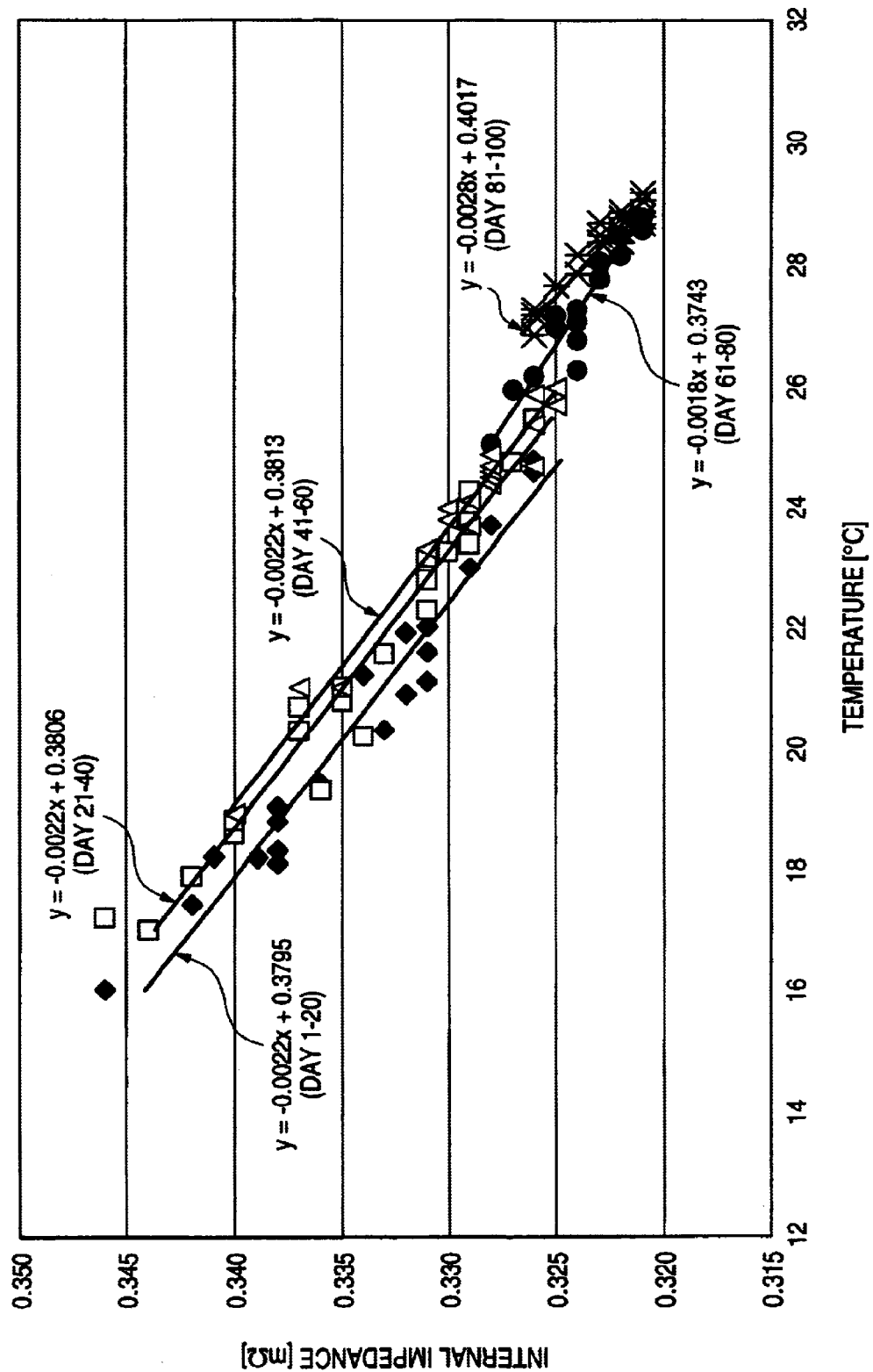
FIG. 11 is a graph showing an example of the correlation between the internal impedance of the lead acid battery and the temperature.

Next, to find the temperature correction coefficient of the internal impedance of the lead acid battery 4, the correlation between the internal impedance and the temperature is used. FIG. 11 is a graph to show an example of the correlation between the internal impedance and the temperature. It shows the correlation between the internal impedance and the temperature of a specific lead acid battery 4 during 220 days.

In FIG. 11, actual data is indicated by dots and an approximate curve is indicated by a line. In the embodiment, the approximate curve is used as the temperature correction coefficient to correct the internal impedance of the lead acid battery 4 based on the temperature. As in FIG. 11, it is seen that the relationship between the internal impedance and the temperature is approximated almost linearly.

Actually, if about 15 pieces of data are obtained, it is possible to find the correlation between the internal impedance and the temperature of the lead acid battery 4.

It is not necessary to find the temperature correction coefficient every unit time period (20 days in FIG. 11). The temperature correction coefficient may be found from the measurement data in the most recent time period measuring the internal impedance of the lead acid battery 4 and the internal impedance of the lead acid battery 4 may be corrected based on the temperature.

Figure 12:
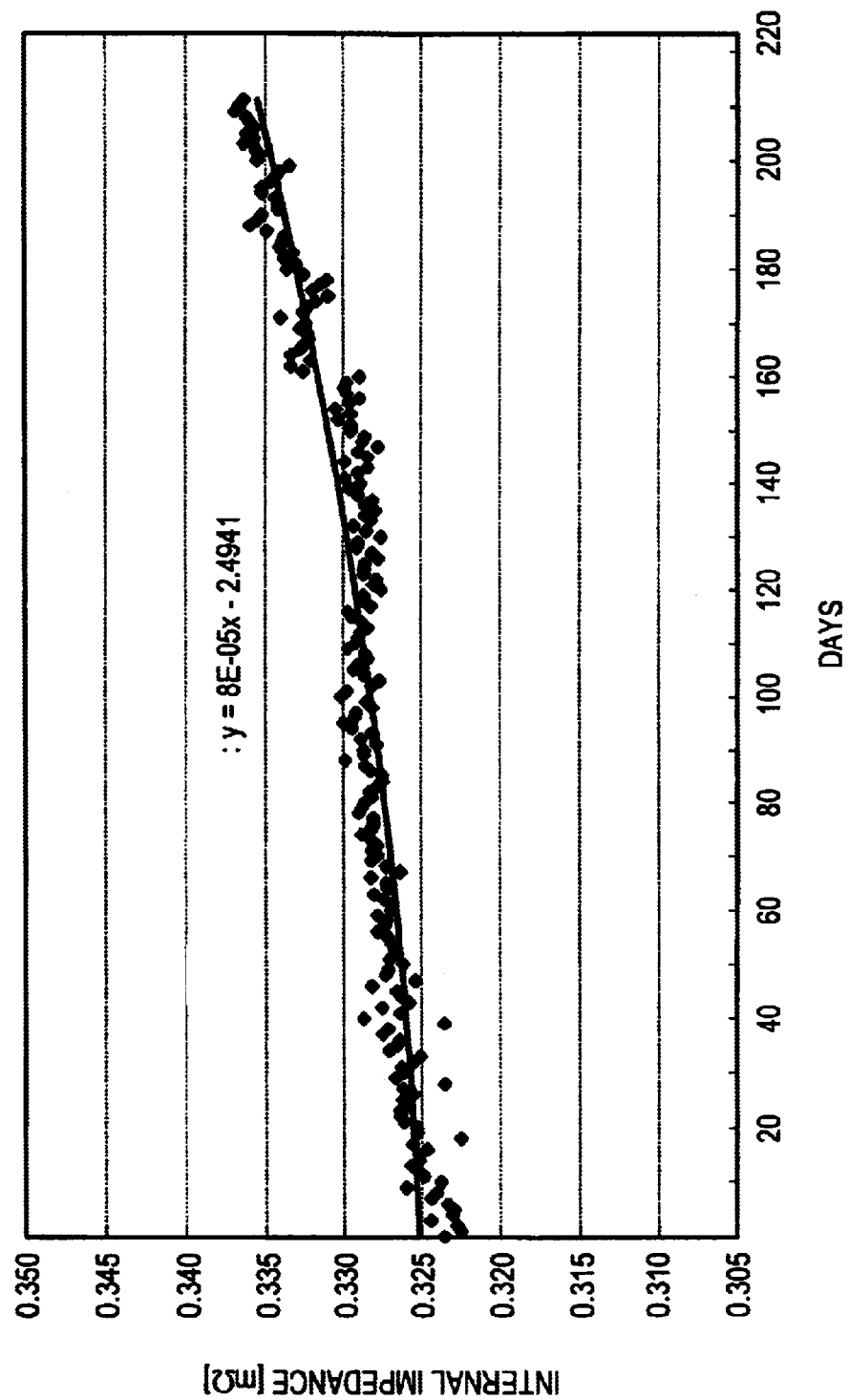
FIG. 12 is a graph to show an example of temperature 25° C. terms of the internal impedance in the embodiment of the invention.

Lastly, the measurement result of the internal impedance of the lead acid battery 4 corrected based on the temperature according to the found temperature correction coefficient is shown. FIG. 12 is a graph to show an example the internal impedance at temperature 25° C. In this figure, the data corrected based on the temperature is indicated by dots and the approximate curve of the data corrected based on the temperature is indicated by a line.

It is seen that the approximate curve is shaped like a parabola which is slightly downward convex.

In the embodiment, the internal impedance of the lead acid battery is thus corrected to a value at the reference temperature based on the measurement data, so that the measurement result of the internal impedance of the lead acid battery can be precisely corrected based on the temperature. It is also made possible to use the result corrected based on the temperature to grasp the lifetime of each of the lead acid batteries making up the lead acid battery unit 12, and maintenance and management of the lead acid batteries 1 can also be optimized.

Although the present invention has been shown and described with reference to specific preferred embodiments, various changes and modifications will be apparent to those skilled in the art from the teachings herein. Such changes and modifications as are obvious are deemed to come within the spirit, scope and contemplation of the invention as defined in the appended claims.

What is claimed is:

1. A method of monitoring a state of a battery, comprising:
    determining a threshold value of an internal impedance of the battery; preparing an expression indicating a correlation between a residual capacity of the battery and an internal impedance of the battery when the internal impedance is greater than the threshold value;
    measuring the internal impedance of the battery;
    determining an initial value of the residual capacity of the battery when the measured internal impedance is less than or equal to the threshold value; and
    monitoring a value of the residual capacity with the expression when the measured internal impedance is greater than the threshold value.

2. A system of monitoring a state of a battery, comprising:
    a storage for storing a predetermined expression for calculating a correlation between a residual capacity of the battery and an internal impedance of the battery when the internal impedance of the battery is greater than a predetermined threshold value;
    an instrument for measuring the internal impedance of the battery; and
    a monitor for monitoring the residual capacity of the battery with the predetermined expression when the measured internal impedance is greater than the threshold value, and determining an initial value of the residual capacity of the battery when the measured internal impedance is less than or equal to the threshold value.

3. A method of monitoring a state of a battery, comprising:
    measuring an internal impedance of the battery each time a first time period is elapsed;
    storing the measured internal impedance as time-serial impedance data;
    monitoring a residual capacity of the battery;

gathering the time-serial impedance data during a second time period prior to a time point at which the monitored residual capacity is less than or equal to a threshold value;

obtaining an expression for calculating a correlation between the internal impedance and the residual capacity based on the gathered time-serial impedance data; and predicting a residual lifetime of the battery based on the obtained expression.

4. The monitoring method as set forth in claim 3, wherein the threshold value is 85% of an initial capacity of the battery.

5. A method of monitoring a state of a battery, comprising:

measuring an internal impedance of the battery each time a first time period is elapsed;

storing the measured internal impedance as time-serial impedance data;

obtaining an average value of the time-serial impedance data each time a second time period is elapsed;

comparing an average value of a certain second time period and a preceding second time period to obtain a changing rate of the average value; and generating an alarm when the obtained changing rate is greater than or equal to a predetermined value.

6. A method of monitoring a state of a battery, comprising:

measuring an internal impedance of the battery each time a first time period is elapsed;

storing the measured internal impedance as time-serial impedance data;

obtaining an average value of the time-serial impedance data each time a second time period is elapsed;

obtaining an expression indicating a correlation between the average value and an elapsed time in the second time period, based on the time-serial impedance data each time the second time period is elapsed;

predicting a time point at which a changing rate of the average value compared to at least one of a preceding average value is greater than or equal to a predetermined value, based on the expression; and displaying the predicted time point as a residual lifetime of the battery.

7. A system of monitoring a state of a battery, comprising:

an instrument for measuring an internal impedance of the battery each time a first time period is elapsed;

a storage for storing the measured internal impedance as time-serial impedance data;

a monitor for monitoring a residual capacity of the battery; and a calculator for gathering the time-serial impedance data during a second time period prior to a time point at which the monitored residual capacity is less than or equal to a threshold value; obtaining an expression indicating a correlation between the internal impedance and the residual capacity based on the gathered time-serial impedance data; and predicting a residual lifetime of a battery based on the obtained expression.

8. The monitoring system as set forth in claim 7, wherein the threshold value is 85% of an initial capacity of the battery.

9. A system of monitoring a state of a battery, comprising:

an instrument for measuring an internal impedance of the battery each time a first time period is elapsed;

a storage for storing the measured internal impedance as time-serial impedance data;

a calculator for obtaining an average value of the time-serial impedance data each time a second time period is elapsed;

a comparator for comparing an average value of a certain second time period and a preceding second time period to obtain a changing rate of the average value; and an alarm for generating an alarm when the obtained changing rate is greater than or equal to a predetermined value.

10. A system of monitoring a state of a battery, comprising:

an instrument for measuring an internal impedance of the battery each time a first time period is elapsed;

a storage for storing the measured internal impedance as time-serial impedance data;

a calculator for obtaining an average value of the time-serial impedance data each time a second time period is elapsed; obtaining an expression indicating a correlation between the average value and an elapsed time in the second time period, based on the time-serial impedance data each time the second time period is elapsed; and predicting a time point at which a changing rate of the average value is greater than or equal to a predetermined value, based on the expression; and a display for displaying the predicted time point as a residual lifetime of the battery.

11. A method of measuring an internal impedance of a battery, comprising:

measuring an internal impedance and a temperature of the battery at the same time;

storing the measured internal impedance and the measured temperature as time-serial impedance data and time-serial temperature data;

obtaining a correction coefficient based on a correlation between the time-serial impedance data and the time-serial temperature data during a predetermined time period; and correcting the measured internal impedance with the correction coefficient as a value at a reference temperature.

12. A system for measuring an internal impedance of a battery, comprising:

an instrument for measuring an internal impedance and a temperature of the battery at the same time;

a storage for storing the measured internal impedance and the measured temperature as time-serial impedance data and time-serial temperature data;

a calculator for obtaining a correction coefficient based on a correlation between the time-serial impedance data and the time-serial temperature data during a predetermined time period; and a corrector for correcting the measured internal impedance with the correction coefficient as a value at a reference temperature.

13. The method of measuring an internal impedance of a battery of claim 1, wherein the measuring comprises measuring the internal impedance and a temperature of the battery at the same time.

14. The method of measuring an internal impedance of a battery of claim 13, further comprising storing the measured internal impedance and the measured temperature as time-serial impedance data and time-serial temperature data.

15. The method of measuring an internal impedance of a battery of claim 14,
further comprising obtaining a correction coefficient based on a correlation between the time-serial impedance data and the time-serial temperature data during a predetermined time period.

16. The method of measuring an internal impedance of a battery of claim 15,
further comprising correcting the measured internal impedance with the correction coefficient as a value at a reference temperature.

17. The system for measuring an internal impedance of a battery of claim 2,
wherein the instrument measures the internal impedance and a temperature of the battery at the same time.

18. The system for measuring an internal impedance of a battery of claim 17,
wherein the storage stores the measured internal impedance and the measured temperature as time-serial impedance data and time-serial temperature data.

19. The system for measuring an internal impedance of a battery of claim 18,
wherein the monitor obtains a correction coefficient based on a correlation between the time-serial impedance data and the time-serial temperature data during a predetermined time period.

20. The system for measuring an internal impedance of a battery of claim 19, further comprising a corrector for correcting the measured internal impedance with the correction coefficient as a value at a reference temperature.

21. The method of measuring an internal impedance of a battery of claim 3,
wherein the measuring comprises measuring the internal impedance and a temperature of the battery at the same time.

22. The method of measuring an internal impedance of a battery of claim 21,
wherein the storing comprises storing the measured internal impedance and the measured temperature as time-serial impedance data and time-serial temperature data.

23. The method of measuring an internal impedance of a battery of claim 22,
wherein the obtaining comprises obtaining a correction coefficient based on a correlation between the time-serial impedance data and the time-serial temperature data during a predetermined time period.

24. The method of measuring an internal impedance of a battery of claim 23,
further comprising correcting the measured internal impedance with the correction coefficient as a value at a reference temperature.

25. The method of measuring an internal impedance of a battery of claim 5,
wherein the measuring further comprises measuring the internal impedance and a temperature of the battery at the same time.

26. The method of measuring an internal impedance of a battery of claim 25,
wherein the storing further comprises storing the measured internal impedance and the measured temperature as time-serial impedance data and time-serial temperature data.

27. The method of measuring an internal impedance of a battery of claim 26,
wherein the obtaining further comprises obtaining a correction coefficient based on a correlation between the time-serial impedance data and the time-serial temperature data during a predetermined time period.

28. The method of measuring an internal impedance of a battery of claim 27,
further comprising correcting the measured internal impedance with the correction coefficient as a value at a reference temperature.

29. The method of measuring an internal impedance of a battery of claim 6,
wherein the measuring further comprises measuring the internal impedance and a temperature of the battery at the same time.

30. The method of measuring an internal impedance of a battery of claim 29,
wherein the storing further comprises storing the measured internal impedance and the measured temperature as time-serial impedance data and time-serial temperature data.

31. The method of measuring an internal impedance of a battery of claim 30,
wherein the obtaining further comprises obtaining a correction coefficient based on a correlation between the time-serial impedance data and the time-serial temperature data during a predetermined time period.

32. The method of measuring an internal impedance of a battery of claim 31,
further comprising correcting the measured internal impedance with the correction coefficient as a value at a reference temperature.

33. The system for measuring an internal impedance of a battery of claim 7,
wherein the instrument measures the internal impedance and a temperature of the battery at the same time.

34. The system for measuring an internal impedance of a battery of claim 33,
wherein the storage stores the measured internal impedance and the measured temperature as time-serial impedance data and time-serial temperature data.

35. The system for measuring an internal impedance of a battery of claim 34,
wherein the calculator obtains a correction coefficient based on a correlation between the time-serial impedance data and the time-serial temperature data during a predetermined time period.

36. The system for measuring an internal impedance of a battery of claim 35, further comprising a corrector for correcting the measured internal impedance with the correction coefficient as a value at a reference temperature.

37. The system for measuring an internal impedance of a battery of claim 9,
wherein the instrument measures the internal impedance and a temperature of the battery at the same time.

38. The system for measuring an internal impedance of a battery of claim 37,
wherein the storage stores the measured internal impedance and the measured temperature as time-serial impedance data and time-serial temperature data.

39. The system for measuring an internal impedance of a battery of claim 38,
wherein the calculator obtains a correction coefficient based on a correlation between the time-serial impedance data and the time-serial temperature data during a predetermined time period.

40. The system for measuring an internal impedance of a battery of claim 39, further comprising a corrector for correcting the measured internal impedance with the correction coefficient as a value at a reference temperature.

* * * * *